United States Patent [19]

Kees, Jr. et al.

[11] Patent Number: 4,961,743
[45] Date of Patent: Oct. 9, 1990

[54] TORSION SPRING

[75] Inventors: George Kees, Jr., Alexandria, Ky.; Charles B. Worrick, III, Hanson; John A. Santangelo, East Freetown, both of Mass.

[73] Assignee: Codman & Shurtleff, Inc., Randolph, Mass.

[21] Appl. No.: 292,986

[22] Filed: Jan. 3, 1989

[51] Int. Cl.$^5$ .............................................. A61B 17/08
[52] U.S. Cl. .................................... 606/158; 606/151; 606/157
[58] Field of Search ....................... 606/151, 157, 158; 16/75; 267/154, 155, 156, 275; 140/103

[56] References Cited

U.S. PATENT DOCUMENTS

3,827,438  8/1974  Kees, Jr. ............................ 606/158
4,796,625  1/1989  Kees, Jr. ............................ 606/158

Primary Examiner—Robert A. Hafer
Assistant Examiner—BethAnne Cicconi
Attorney, Agent, or Firm—Donal B. Tobin

[57] ABSTRACT

A torsion spring with a coil portion having extensions extending from the ends of the coil for receiving forces for torquing the spring. The spring provides a more balanced stress distribution about the coil which in the preferred embodiment include a region of increased cross-sectional area on one side of the coil and a region of decreased cross-sectional area across the coil from the region of increased cross-sectional area and smooth contouring of the coil between these two regions. A particular use of the torsion spring of the present invention is in a torsion spring-type aneurysm clip for providing more uniform stress distributions about the coil portion of the aneurysm clip and for permitting the aneursym clip to open wider so that it may be used on larger aneurysms.

9 Claims, 5 Drawing Sheets

TORSION SPRING

FIELD OF THE INVENTION

The present invention relates to a torsion spring and particularly to a torsion spring with a more balanced stresses distribution in the coil portion of the torsion spring, and more particularly to an aneurysm clip employing such a torsion spring.

BACKGROUND OF THE INVENTION

A torsion spring has a coil portion with one or more coils usually forming a generally circular annulus with a coil axis and a transverse diameter generally perpendicular to the coil axis. Some torsion springs may even have less than a full coil. The ends of the coil usually extend from the coil to receive forces that induce torque in the spring. These extensions usually extend in a generally tangential direction but can extend at any angle from the coil or any place about the circumference of the coil depending upon the use to which the torsion spring is put. When a moment is applied to the torsion spring, (a moment being the applied force to the extension multiplied by the distance from the centerline of the coil where the force is applied to the extension), the coil deflects and the material from which it is made is placed under stress. When the moment is relaxed, the coil relaxes and returns to its original shape. As deflection increases, stress increases toward the elastic limit of the material. If the elastic limit is exceeded the coil retains a permanent deflected even after the moment is released. Maximum desired deflection of a coil for a particular applied moment is an important criterion for spring design. In conventional spring designs, one can select material, shape, cross section and the number of coils, among other things, to provide the desired spring performance.

In certain applications, for example, where the force must be applied close to the center line of the coil or where the coil must be used in a confined space so that shape and number of coils are limited, even small deflections can cause large variations in stress at different points around the circumference of the coil. In such applications, portions of the coil can approach the elastic limit even at small deflections.

If conventional torsion springs which have force receiving extensions facing the same side of the coil axis are deflected, high moments and thus high stresses will be experienced on that part of the coil away from the extensions and lower moments and thus lower stresses will be experienced on that part of the coil close to the extensions. The bulk of material in the low stress area may stiffen the coil. The added stiffness in this area can make it harder for this area to deflect. This stiffness can cause deflection in some other area of the coil and possibly increase the tendency of other portions of the coil to approach the elastic limit of the material. We believe that the extra bulk of material in the lower stressed area of the coil can exaggerate the non-uniform stress distribution and actually decrease the effectiveness of the spring. It would be desirable to have a torsion spring with a more uniform stress distribution so that a single torsion spring could be used over a wider variety of angular deflections.

One application of particular interest to us is a torsion spring aneurysm clip where the force receiving extensions face the same side of the coil axis to form the shoulders of aneurysm clip.

An aneurysm is a permanent dilitation of the wall of a blood vessel usually caused by weakening of the wall as a result of some pathological condition. In laymen's terms, the wall weakens and pressure in the vessel causes the wall to expand into a balloon appendage on the side of the vessel. The balloon often has a neck portion extending from the wall and an expanded portion connected to the neck, although an aneurysm may take on various shapes.

One way of treating an aneurysm is to apply a clip to seal off the neck portion of the aneurysm close to the blood vessel wall so that blood pressure will not be exposed to the weakened expanded portion of the aneurysm. Thus, the possibility of the aneurysm bursting is reduced and hopefully eliminated. It is hoped that the clip will seal off the weakened portion of the wall so that the blood vessel can heal.

In the past, torsion spring-type aneurysm clips have been used to effectively seal off certain aneurysms. An aneurysm clip of the kind discussed in the present application is similar to that shown in U.S. Pat. No. 3,827,438 but this patent does not suggest or disclose the special torsion spring discussed in the present patent application. These torsion spring clips have a coil portion with a first arm extending from one end of the torsion spring and offset to one side of the coil and a second arm extending from the other end of the torsion spring offset on the same side of the coil. Each of the first and second arms has a shoulder portion, a cross over portion and a jaw portion. When the shoulder portions are moved toward one another (with a special forcep) so as to torque the torsion spring, the jaw portions move away from each other toward an open position so that the aneurysm can be grasped between the two confronting jaw portions to seal off the aneurysm.

An aneurysm clip designer must deal with several design constraints. Since aneurysm clips are used in the brain and are often permanently implanted they should be as small as possible so that they may be used in very confined spaces. The implant must be biocompatible thus only a few materials, like high strength, high alloy metals are recommended for use. The jaw closing force must be large enough to seal off the aneurysm and not be dislodged or otherwise effected by changes in pressure in the blood vessel. Aneurysm clip jaws also have various shapes, lengths and angles for use with different kinds of aneurysms but the coil spring portions of these aneurysm clips are uniform so as to fit into one sized forcep. It is also desirable that the clip be light weight so as not to pull on the blood vessel to which it is attached.

Thus, the aneurysm clip designer must deal with limits on the clip material, size, weight and force requirements.

An aneurysm clip designer wishes to obtain the maximum jaw deflection from a particular configuration torsion spring. In a conventional torsion spring application, if one wanted larger deflections one would apply the forces at a point farther away from the center line of the coil spring to obtain a higher moment. That is inconvenient for aneurysm clips because it increases the size of the clip and could require the use of different forceps. Some giant aneurysms require clips whose jaws open wider than most available aneurysm clips will permit. Consequently, many surgeons do not attempt to use torsion type aneurysm clips to seal off such giant aneurysms. If one attempts to open the jaws of a conventional clip a sufficient amount to accommodate a giant aneurysm, it is possible for the coil material on the side of the torsion spring away from the jaws to experience stresses beyond its elastic limit and for the bulk of material on the side of the coil close to the jaws to stiffen the torsion spring and exaggerate the uneven stress distribution.

It would be desirable to have a clip which could use the same coil portion but could open wide enough to accept large and small aneurysms without going beyond the elastic limit of the metal of which the clip is made.

SUMMARY OF THE INVENTION

The present invention relates to a torsion spring with a coil portion having a coil axis and a transverse coil diameter generally perpendicular to the coil axis and having extensions from the ends of the coil and which has a means for providing a more balanced stress about the circumference of the coil when the spring is torqued. The preferred means for providing this balanced stress distribution is to vary the cross sectional area of the metal from which the torsion spring is made. The metal may be formed into a desired shape which has a substantially uniform thickness in a direction parallel to the coil axis and a varying width in a direction generally perpendicular to the coil axis so that when the metal is formed into a coil spring, the center of the enclosure defining the inside diameter of coil spring is offset from the center of the enclosure defining the outside diameter of the coil spring. Thus, one side of the coil spring will be wide to reduce the potential for higher stress levels when the spring is torqued and the other side of the spring will be narrow to more readily deflect and distribute stress more uniformly when the spring is torqued. The surface defining the inside diameter of the coil spring portion is smoothly contoured from the narrow to the wide portion to a generally circular shape. The torsion spring of the present invention provides a more balanced distribution of stresses about the circumference of the coil.

Alternative means for adjusting the cross-sectional area at high and low stress points around the circumference of the coil can be used. Instead of having a uniform thickness in a direction parallel to the coil axis and a varying width in a direction perpendicular to the coil axis, one can vary the thickness in a direction parallel to the coil axis and keep a uniform width in a direction perpendicular to the coil axis. Both of these embodiments suggest a rectangular cross-section for the coil material. Although a rectangular cross-section is preferred it is not necessary and a variety of coil cross-sections, for example, circles or ellipses can be used. In the preferred embodiment the coil is wound in a generally circular configuration, but any convenient shape can be used and still take advantage of the benefits of the present invention. Throughout this application we will describe the coil in terms of a coil axis and a coil diameter but these terms are not meant to imply that the coil may only be circular. We are merely describing the direction axially through the space defined by the coil windings and a direction transverse to the coil windings.

In the preferred embodiment, the extensions from the end of the coil portion of the torsion spring extend tangentially from the coil spring and provide a means to receive forces for torquing the spring. It is not required that these extensions extend tangentially but may be at any angle and may be placed at any location around the circumference of the coil portion depending upon the intended use for the torsion spring.

The torsion spring of the present invention can be used to provide an aneurysm clip with a more balanced stress distribution about the circumference of the torsion spring portion of the aneurysm clip. The aneurysm clip has a torsion spring having at least one coil or a partial coil aligned about a coil axis and first and second arms extending from opposite ends of the torsion spring and offset on one side of the coil axis. Each of the first and second arms has a shoulder portion disposed in opposed spaced-apart relationship and a jaw portion disposed in confronting relationship. The first and second arms cross over one another so that when the shoulder portions are moved toward one another, for example, by the use of an applier tool, the torsion spring is torqued and the jaw portions of each arm move away from one another to an open position ready to be placed about an aneurysm. The aneurysm clip of the present invention includes means for providing a substantially balanced stresses about the circumference of the coil portion.

In the preferred embodiment of the aneurysm clip of the present invention, the substantially balanced stress distribution is accomplished by providing a non-uniform cross-section coil portion as described above for the torsion spring. These and other features and advantages of the present invention will become more apparent from the following detailed description of the preferred embodiments taken in conjunction with the following drawings.

DETAILED DESCRIPTION OF THE PREFERRED EMBODIMENT

Figure 1:
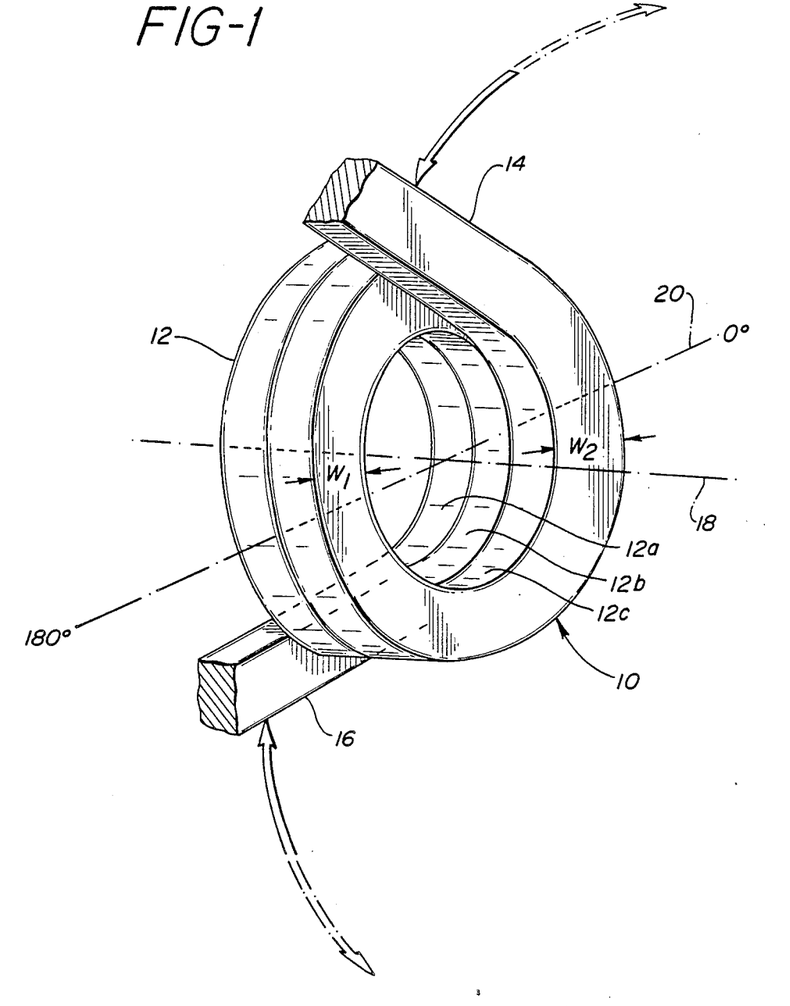
FIG. 1 shows a partial perspective view of the torsion spring of the present invention.

Referring now to FIG. 1, there is shown the torsion spring 10 of the present invention having a coil portion 12 and extension 14 extending from one end of the coil Portion 12 and extension 16 extending from the other end of coil portion 12. Coil portion 12 has a coil axis 18 about which coil 12 is wound and a coil transverse diameter 20 aligned generally perpendicular to coil axis 18.

Figure 6:
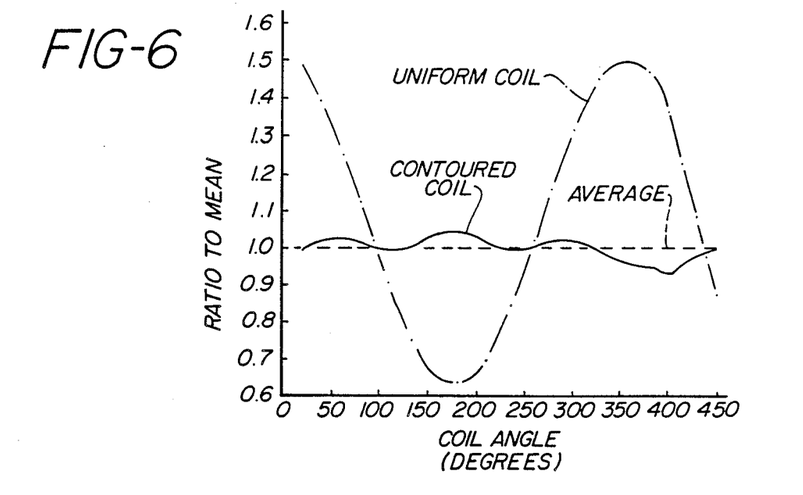
FIG. 6 shows a graPhic representation of stress on the torsion spring of the present invention and convention springs.

The coil spring 10 shown in FIG. 1 has three coils 12a, 12b and 12c. Transverse diameter 20 shows a zero degree (0°) position at the right side of FIG. 1 and a 180° position at the left side of FIG. 1. When viewing FIG. 6, one will note that the horizontal axis shows a coil angle from 0° to 450°. This reflects the stress values on all of coil 12b and part of coil 12c or 12a up to approximately the point where extensions 14 or 16 begin. FIG. 6 represents the stress distribution on more than one turn of torsion spring 10.

In the preferred embodiment of FIG. 1, extensions 14 and 16 extend generally tangentially from coil portion 12 and extend on the same side of the coil axis 18. Extensions 14 and 16 are used to receive the forces for torquing torsion spring 10. Extensions 14 and 16 need not extend tangentially but may extend in any direction suitable for the intended use of torsion spring 10. Also extensions 14 and 16 need not extend on the same side of coil axis 18 but may be positioned at any circumferential position about coil portion 12 suitable for the intended use of torsion spring 10.

Figure 5:
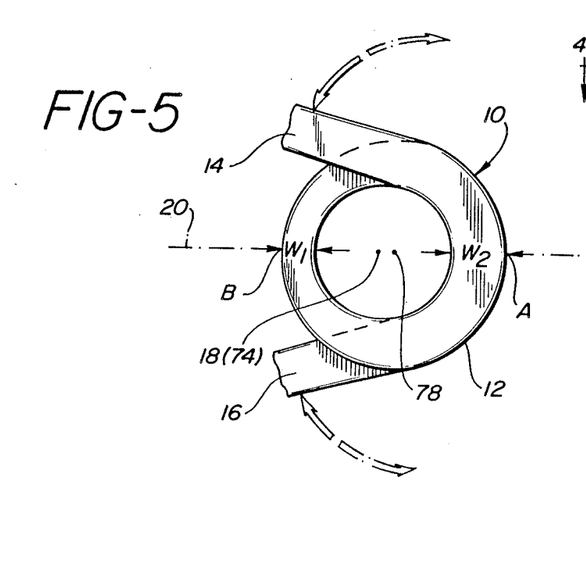
FIG. 5 shows a partial side elevation view of the torsion spring of the present invention.

Referring now to FIG. 5, where torsion spring 10 is shown in side elevation, coil transverse diameter 20 is shown together with coil axis 18. One will note that the width of coil portion 12 at area A is wider than that of coil portion 12 at diametrically opposed area B. The cross section of coil portion 12 is smoothly contoured between area A and B so that the resulting inside diameter of coil portion 12 is generally circular but its center 74 is offset from the center 78 of the outside diameter of coil portion 12. This novel feature of the present invention is intended to provide balanced stresses on coil portion 12 at diametrically opposed cross-sectional areas A and B and around the circumference of coil portion 12. It has been found that when extensions 14 and 16 are moved in the direction shown a large amount very large stresses are placed on coil portion 12 at cross-section area A which can sometimes exceed the elastic limit of the metal from which torsion spring 10 is made. The increased stress at area A can be accomodated by the increased material in that portion of coil portion 12. At the same time material is removed from coil portion 12 at cross-sectional area B so that the additional material that would be present in a conventional coil spring does not stiffen torsion spring 10 and exaggerate the uneven stress distribution as explained above. Conventional coil springs have a uniformed dimension in a direction perpendicular to coil axis 18 about the entire circumference of coil portion 12. Contouring coil portion 12 to make a larger cross-section at area A and a smaller cross-section at diametrically opposed area B provides a means for balancing the stresses in torsion spring 10. This balancing of stresses permits torsion spring extensions 14 and 16 to move through a greater rotational arc and accept greater deflection without subjecting the metal from which torsion spring 10 is made to stresses beyond the elastic limit.

Referring again to FIG. 1, it will be noted that the thickness of the material of coil portion 12 in a direction parallel to coil axis 18 is substantially uniform about the circumference of coil portion 12. The width of coil portion 12 in a direction perpendicular to coil axis 18 varies. Since the cross-sectional area is the important feature, the width of coil portion 12 could be uniform in a direction perpendicular to coil axis 18 and the thickness in a direction parallel to coil axis 18 could vary. Furthermore the cross-section need not be rectangular but could be any convenient shape that provided a means for balancing the stress around the circumference of coil portion 12.

Figure 4A:
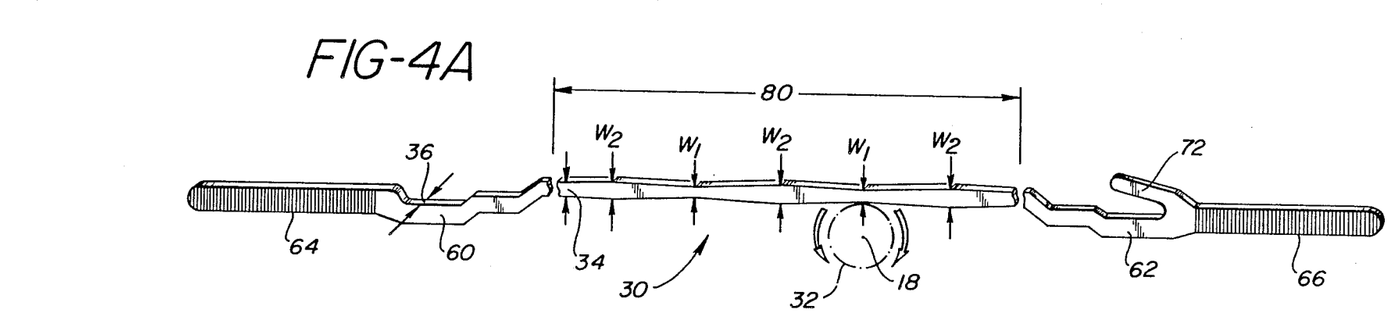
FIG. 4A shows a perspective view, partly in section, of a flat piece of metal before it is bent into an aneurysm clip of the present invention.

Referring now to FIG. 4A, there is shown a flat bar or sheet of metal 30 from which torsion spring 10 is made. Portion 80 of sheet 30 is made into torsion spring 10. Additional structure, for example, the shoulders and jaws of an aneurysm clip can be added to sheet 30 and formed by well known means. We will first discuss making torsion spring 10 and later discuss the use of torsion spring 10 as part of an aneurysm clip.

Torsion spring 10 can be made from sheet 30 by well known means usually by bending and the method of manufacture will not be discussed since it is believed that that method is well known to those skilled in this art. In the preferred embodiment, portion 80 of sheet 30 has a generally rectangular shape, however, the initial shape of the sheet can vary depending upon the intended use of torsion spring 10. The starting material could be rectangular or square in cross-section or could even be round or elliptical wire stock. Sheet material is preferably formed by well-known processes of die stamping or by a similarly well-known process of electric discharge machining or it could be formed by forging or grinding or other forming method.

In the preferred embodiment, the means used to balance the stresses about the circumference of coil spring 12 includes adjusting the geometry of sheet 30 which is made of a substantially uniform piece of metal preferably high strength, high alloy metal. However, other methods of adjusting the effective stresses at different points on coil portion 12 could be used, for example, one could use different heat treating methods at different points along sheet 30 or one could even provide different metal alloys at different places along sheet 30.

Figure 4B:
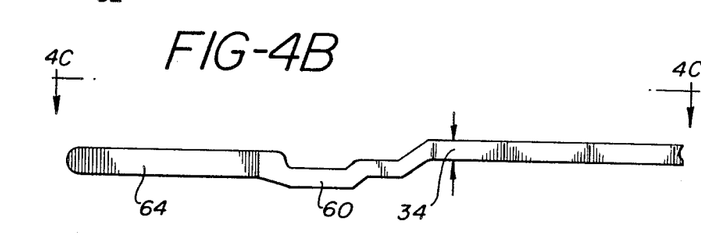
FIG. 4B shows a partial elevation view of a different embodiment of the aneurysm clip of the present invention.
Figure 4C:
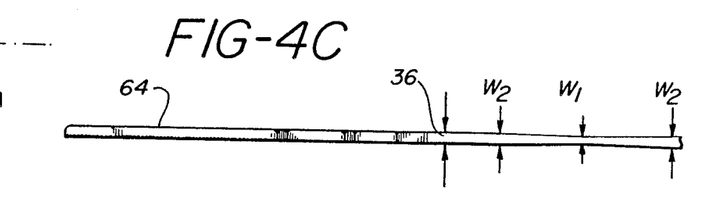
FIG. 4C shows a partial plan view of the embodiment of FIG. 4B.

Still referring to FIG. 4A, there is shown in phantom a jig 32 about which portion 80 of sheet 30 may be bent to form coil portion 12. Coil axis 18 is aligned with the center of curvature of jig 32 so that one can see from FIG. 4A the orientation of portion 80 of sheet 30 when it is formed into coil portion 12. The thickness 36 of portion 80 of sheet 30 in a direction generally parallel to coil axis 18 is substantially uniform. The width 34 of portion 80 of sheet 30 in a direction generally perpendicular to coil axis 18 varies to provide varying cross-sectional areas between areas A and B in FIG. 5 discussed above. In FIG. 4B the width of portion 80 of sheet 30 in a direction generally perpendicular to coil axis 18 is substantially uniform and the thickness (see FIG. 4C) in a direction generally parallel to axis 18 varies to provide the varying cross-sectional areas between areas A and B.

In FIG. 4A sheet 30 includes more than just coil spring portion 12 of a torsion spring 10 but also shows portions of an aneurysm clip which extend from torsion spring 10. The use of torsion spring 10 in an aneurysm clip will now be discussed in conjunction with FIGS. 2, 3A and 3B.

Figure 2:
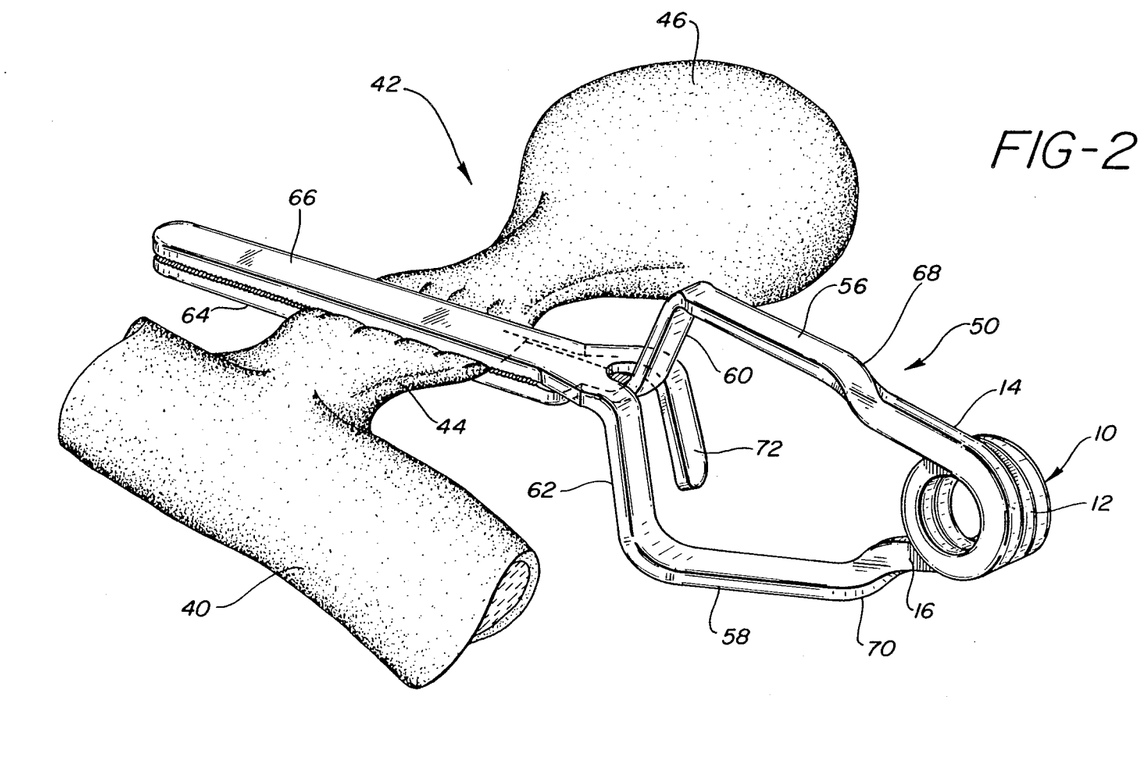
FIG. 2 shows a perspective view of an aneurysm clip employing the torsion spring of the present invention with the clip placed on an aneurysm.

Referring now to FIG. 2, there is shown a portion of a blood vessel 40 with an aneurysm 42 extending from the side wall of blood vessel 40. The particular aneurysm 42 shown in FIG. 2 includes a neck portion 44 and a balloon expansion portion 46. This is only meant to be illustrative of a particular kind of aneurysm. Aneurysms come in many sizes and shapes requiring a wide variety of aneurysm clips. One particular design of aneurysm clip 50 suitable for use with the type of aneurysms shown in FIG. 2, is shown attached to neck portion 44 of aneurysm 42.

Figure 3A:
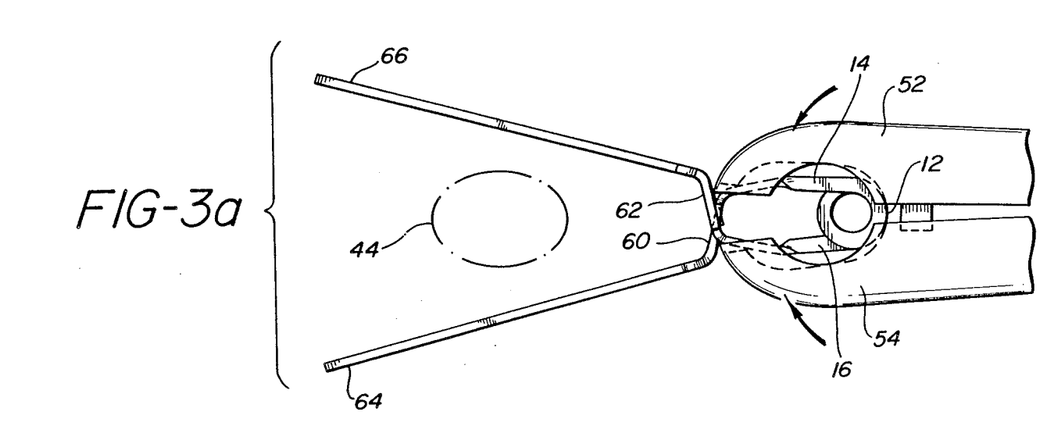
FIG. 3A shows an aneurysm clip employing the torsion spring of the present invention with the jaws open.
Figure 3B:
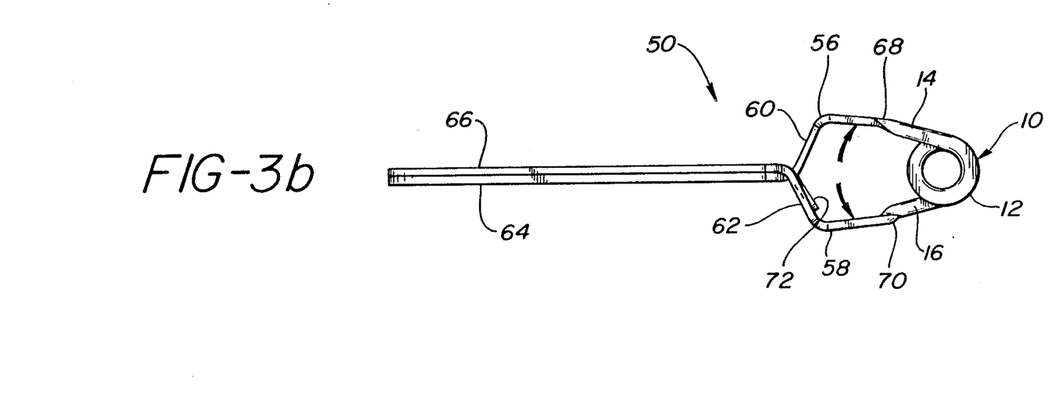
FIG. 3B shows an aneurysm clip employing the torsion spring of the present invention with the jaws closed.

Referring now to FIGS. 3A and 3B, there is shown an aneurysm clip 50 employing torsion spring 10 of the present invention lodged in the jaws 52 and 54 of an applying instrument (only partially shown) and shown in the open position. Extensions 14 and 16 extend from coil portion 12 and are intergally formed into shoulder portions 56 and 58 which include respective cross over portions 60 and 62. Jaw portions 64 and 66 are intergally formed to cross over portions 60 and 62. In aneurysm clip 50, extensions 14 and 16 have a generally rectangular cross-section whose dimension is smaller in a direction generally parallel to coil axis 18. When torsion spring 10 is used with an aneurysm clip, it is desirable to have the broader dimension of the material from which the clip is made on the confronting surfaces of jaws 64 and 66. This requires the material to be twisted 90°. Each shoulder 56 and 58 has a 90° twist at points 68 and 70. This 90° twist can be done all in one place as in the preferred embodiment shown in FIG. 3B or it can be made in a series of smaller steps as desired. Aneurysm clip 50 also has an anti-scissors projection extending from one jaw (for example jaw 66) in a direction toward coil portion 12 to reduce the possibility of misalignment of jaws 64 and 66 as they are opened and closed.

In FIG. 3B aneurysm clip 50 is shown with jaws 64 and 66 closed.

The center of curvature of the enclosure defining the inside diameter of coil portion 12 is located at point 74. The center of the enclosure defining the outside diameter of coil portion 12 is located at point 78 offset from point 74. The variance in area between cross-sectional areas A and B is responsible for the offset between points 74 and 78.

The Applicants have found that using torsion spring 10 of the present invention with aneurysm clip 50 permits jaws 64 and 66 to be opened a wider extent without exceeding the elastic limit of the material.

In operation, a surgeon grasps aneurysm clip 50 with jaws 52 and 54 of an instrument and operates the instrument so as to rotate extensions 14 and 16 toward one another so as to induce torque into coil portion 12 and permit jaws 64 and 66 to open. Aneurysm clip 50 is then inserted about neck portion 44 of aneurysm 42. When the surgeon releases the instrument, jaws 64 and 66 close tightly about neck prtion 44 and close off the aneurysm 42.

Figure 7A:
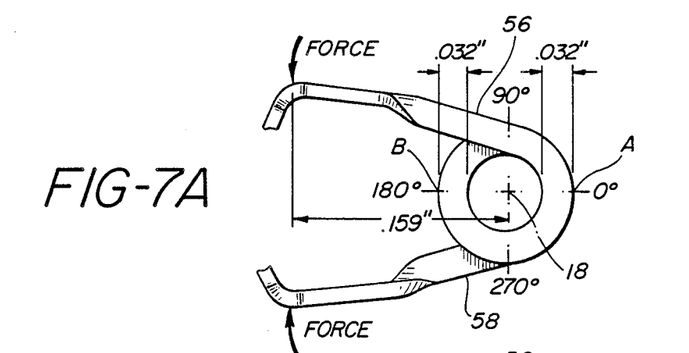
FIG. 7A is a schematic representation of a conventional clip with uniform cross section.
Figure 7B:
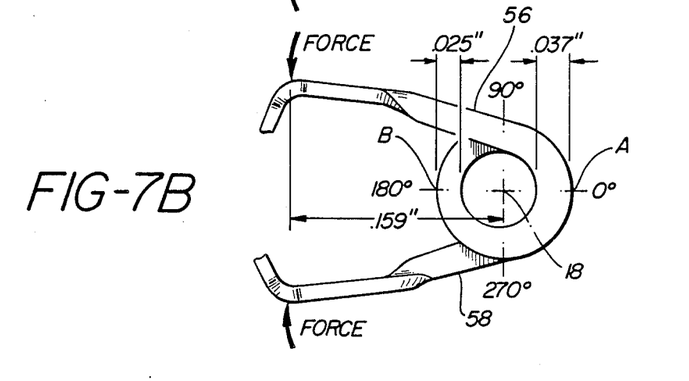
FIG. 7B is a schematic representation of the contoured clip of the present invention.

Referring now to FIG. 6, there is shown a graphic comparison of the stresses at various angular positions on a conventional coil with a uniform cross sectional area as shown in FIG. 7A compared to the stresses at the same points on the contoured coil of the present invention as shown in FIG. 7B calculated with a computer simulation. In FIG. 6 a dimensionless stress ratio is shown on the vertical axis. The angular position where the stress exists around the coil of the torsion spring is shown on the horizontal axis. As explained above, the horizontal axis shows angular positions from 0° to 450° moving from the 0° position on coil 12b around to where extension 14 begins on coil 12c or where extension 16 begins on coil 12a (see FIG. 1). In FIGS. 7A and 7B the 0° position is shown at cross sectional area A, the 90° position is shown as the top vertical position, the 180° position is shown at cross sectional area B and the 270° position is shown at the bottom position. There are two curves shown in FIG. 6; one for the uniform cross-sectional area coil and one for the contoured coil.

One curve shows the stress at a point on a coil of uniform cross-sectional area divided by the average stress around the uniform coil for the same load. The other curve shows the stress at a point on a contoured coil divided by the average stress on the contoured coil under the same load. These curves yield representative dimensionless parameters which we feel demonstrate the advantages of the contoured coil of the present invention in a generalized fashion.

In the computer simulation, the same force was applied to both the uniform and the contoured clip at shoulders 56 and 58 in FIGS. 7A and 7B in such a way as to move extensions 14 and 16 toward one another. The force was applied to a computer simulated conventional clip shown in FIG. 7A at a point 0.159 inches from coil axis 18 of the uniform coil shown in FIG. 7A. The thickness in a direction parallel to the axis of the coil of uniform coil shown in FIG. 7A is uniform and the width at cross sectional areas A and B of this uniform coil is 0.032 inches. The outside diameter of uniform coil shown in FIG. 7A is 0.153±0.001 inch. The outside diameter of the contoured coil shown in FIG. 7B is 0.153±0.001 inch. The force applied to a computer simulated contoured coil of the present invention was applied at the same distance 0.159 inches from coil axis 18 of the contoured coil at shoulders 56 and 58. The dimensions of the contoured coils shown in FIG. 7B have a uniform thickness in a direction parallel to coil axis 18, a width at cross sectional area B in a direction perpendicular to coil axis 18 of 0.025 inches and a width in cross sectional area A in a direction perpendicular to coil axis 18 equal to 0.037 inches.

The stresses shown in FIG. 6 were computed with a computer simulation. The stresses shown in FIG. 6 are Von Mises principal stresses which are calculated as shown in *Engineering Considerations of Stress, Strain and Strength* by Robert C. Juvinall, (1967 ed.), page 22, McGraw-Hill.

The values shown in FIG. 6 are not intended to represent actual stress values but are meant to demonstrate the comparisons between the distribution of stress around the inside diameter of the two coils shown schematically in FIGS. 7A and 7B. Although the actual value of the stress at any particular point along the curve may vary depending upon the assumptions used in the computer simulation, the comparison is valid and demonstrates the usefulness of the contoured coil of the present invention in providing substantially balanced stresses around the circumference of the coil portion of the torsion spring of the present invention.

The present invention has been described in conjunction with the preferred embodiments. Those skilled in the art will appreciate that many modifications and changes may be made to the preferred embodiments without departing from the present invention. It is, therefore, not intended to limit the present invention except as set forth in the appended claims.

We claim:

1. A torsion spring comprising:
   a coil portion;
   said coil portion having first and second extensions extending from said coil portion and offset to one side of said coil portion to provide means for applying force to said torsion spring; and,
   means for providing substantially balanced stresses around said coil portion when torque is applied to said torsion spring including a non-uniform cross-section for said coil portion said coil portion having a largest cross-section at a point on said coil portion most removed from said one side and a smallest cross-section at a point on said coil portion closest to said one side.

2. The torsion spring of claim 1 wherein said means for providing said balanced stresses includes:
a sheet of metal wound into a coil portion;
said sheet having a substantially uniform thickness aligned, in the coil portion, generally axially to said coil portion; and
said sheet having a varying width aligned, in said coil portion, generally transversely of said coil portion;
said coil portion being contoured by said varying width to provide a maximum cross-sectional area and a minimum cross-sectional area.

3. The torsion spring of claim 1 wherein said extensions extend from said coil portions in the generally tangential direction.

4. The torsion spring of claim 3 wherein said tangential extensions extend to the same side of the coil axis.

5. An aneurysm clip comprising:
a torsion spring having at least one coil portion;
a first arm extending from an end of said coil portion and offset on one side thereof;
a second arm extending from said coil portion and offset on said one side of said coil;
each of said first and second arms having a shoulder portion disposed in opposed, spaced-apart relationship and a jaw portion disposed in confronting relationship;
said arms crossing over one another so that when said shoulder portions are moved toward one another said jaw portions move away from one another to an open position; and,
means for providing substantially balanced stresses around said coil portion;
wherein said coil portion includes a non-uniformed cross-section, said coil portion having a largest cross-section at a point on said coil portion most removed from said jaw portion and a smallest cross-section at a point on said coil portion closest to said jaw portion.

6. The aneurysm clip of claim 5 wherein the means for providing said balanced stresses includes:
a sheet of material suitable to be wound into a coil portion;
said sheet having a substantially uniform thickness aligned, in the coil portion, generally axially of said coil portion; and,
said sheet having a varying width aligned, in said coil portion, generally transversely of said coil portion;
so that when said sheet is formed into a coil portion, said coil portion is contoured to provide a maximum cross-sectional area disposed transversely of a minimum cross-sectional area.

7. The aneurysm clip of claim 5 wherein said torsion spring, said coil portion and said first and second arms are unitary and made of a substantially uniform piece of spring steel.

8. The aneurysm clip of claim 5 wherein said clip is made of a unitary piece of substantially uniform steel formed into an aneurysm clip by bending.

9. The aneurysm clip of claim 5 wherein said means for Providing said balanced stress distribution includes:
a sheet of material suitable to be wound into a coil portion;
said sheet having a varying thickness aligned, in the coil portion, generally axially of said coil portion; and,
said sheet having a substantially uniform width aligned, in said coil portion, generally transversely of said coil portion.

* * * * *